US006248112B1

(12) United States Patent
Gambale et al.

(10) Patent No.: US 6,248,112 B1
(45) Date of Patent: Jun. 19, 2001

(54) IMPLANT DELIVERY SYSTEM

(75) Inventors: Richard A. Gambale, Tyngsboro; John E. Ahern, Melrose, both of MA (US); Michael Parascandola, Londonderry, NH (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/163,884

(22) Filed: Sep. 30, 1998

(51) Int. Cl.⁷ .................................................. A61F 11/00

(52) U.S. Cl. ............................................. 606/108; 606/185

(58) Field of Search ................................. 606/108, 191, 606/195, 194, 198, 185, 220, 186, 206

(56) References Cited

U.S. PATENT DOCUMENTS

| 3,991,750 | 11/1976 | Vickery . |
| 3,995,617 | 12/1976 | Watkins et al. . |
| 4,307,722 | 12/1981 | Evans et al. . |
| 4,503,569 | 3/1985 | Dotter . |
| 4,546,499 | 10/1985 | Possis . |

(List continued on next page.)

FOREIGN PATENT DOCUMENTS

| 296 19 029 U1 | 4/1997 | (DE) . |
| 0 132 387 | 1/1985 | (EP) . |
| 0 363 661 | 4/1990 | (EP) . |
| 0 515 867 A2 | 12/1992 | (EP) . |
| 0 714 640 A1 | 6/1996 | (EP) . |

(List continued on next page.)

OTHER PUBLICATIONS

A. Hassan Khazei et al., Myocardial Canalization, A New Method of Myocardial Revascularization, The Annals of Thoracic Surgery, vol. 6, No. 2, pp. 163–171, Aug. 1968.
Alfred Goldman et al., Experimental Methods for Producing a Collateral Circulation to the Heart Directly from the Left Ventricle, Journals of Thoracic Surgery, vol, 31, No. 3, pp. 364–374, Mar. 1956.

(List continued on next page.)

Primary Examiner—Pedro Philogene
(74) Attorney, Agent, or Firm—Kirkpatrick & Lockhart LLP

(57) ABSTRACT

The present invention provides an implant delivery system for placing interior defining implants in the human body. The devices comprise elongate shafts and a mechanism at the distal end of the shaft for engaging and retaining the implant in place on the shaft during delivery through the vessels and insertion of the distal end of the shaft into tissue. Some embodiments of the devices are configured to have a plurality of implants and configured to deliver the implants sequentially to a plurality of locations. One embodiment employs a flexible outer tube at its distal end that compresses and crinkles to a larger diameter upon being compressed lengthwise to engage the inside surface of the implant. Another embodiment utilizes a tubular delivery shaft having a circular cross section with segments of oval shaped cross sections which serve to engage the inside of implant located on the shaft. A cam slidable within the shaft engages the oval areas, deforming them to a circular shape which permits the implants to be released. Another embodiment provides delivery force by pressurizing fluid filling the shaft lumen to move a plunger at the distal end of the shaft which carries the implant to be delivered. A feature of the invention provides for monitoring of the depth to which an implant is delivered within tissue by monitoring pressure changes experienced near the distal tip of the shaft. Another feature of the delivery devices provides for drug delivery at the implant site by compressing a drug filled bladder by the expansion of an adjoining bladder. Also disclosed is the use of an electromagnetic guidance system to accurately navigate the delivery devices to the implant delivery sites.

9 Claims, 8 Drawing Sheets

U.S. PATENT DOCUMENTS

| | | |
|---|---|---|
| 4,562,597 | 1/1986 | Possis et al. . |
| 4,580,568 | 4/1986 | Gianturco . |
| 4,582,181 | 4/1986 | Samson . |
| 4,641,653 | 2/1987 | Rockey . |
| 4,649,922 | 3/1987 | Wiktor . |
| 4,655,771 | 4/1987 | Wallsten . |
| 4,658,817 | 4/1987 | Hardy et al. . |
| 4,665,918 | 5/1987 | Garza et al. . |
| 4,681,110 | 7/1987 | Wiktor et al. . |
| 4,718,425 | 1/1988 | Tamaka et al. . |
| 4,733,665 | 3/1988 | Palmaz . |
| 4,768,507 | 9/1988 | Fischell et al. . |
| 4,774,949 | 10/1988 | Fogarty . |
| 4,785,815 | 11/1988 | Cohen . |
| 4,813,925 | 3/1989 | Anderson Jr. et al. . |
| 4,852,580 | 8/1989 | Wood . |
| 4,861,330 | 8/1989 | Voss . |
| 4,889,137 | 12/1989 | Kolobow . |
| 4,904,264 | 2/1990 | Scheunemann . |
| 4,917,666 | 4/1990 | Solar et al. . |
| 4,920,980 | 5/1990 | Jackowski . |
| 4,950,227 | 8/1990 | Savin et al. . |
| 4,995,857 | 2/1991 | Arnold . |
| 4,997,431 | 3/1991 | Isner et al. . |
| 5,040,543 | 8/1991 | Badera et al. . |
| 5,042,486 | 8/1991 | Pfeiler et al. . |
| 5,047,028 | 9/1991 | Gian . |
| 5,049,138 | 9/1991 | Chevalier et al. . |
| 5,056,517 | 10/1991 | Fenici . |
| 5,087,243 | 2/1992 | Avitall . |
| 5,098,374 | 3/1992 | Othel-Jacobsen et al. . |
| 5,114,414 | 5/1992 | Buchbinder . |
| 5,158,548 | 10/1992 | Lau et al. . |
| 5,167,614 | 12/1992 | Tessman et al. . |
| 5,172,699 | 12/1992 | Svenson . |
| 5,176,626 | 1/1993 | Soehendra . |
| 5,190,058 | 3/1993 | Jones et al. . |
| 5,256,146 | 10/1993 | Ensminger et al. . |
| 5,266,073 | 11/1993 | Wall . |
| 5,287,861 | 2/1994 | Wilk . |
| 5,290,295 | 3/1994 | Querals et al. . |
| 5,312,456 | 5/1994 | Reed et al. . |
| 5,324,325 | 6/1994 | Moaddeb . |
| 5,366,493 | 11/1994 | Scheiner et al. . |
| 5,372,600 | 12/1994 | Beyar et al. . |
| 5,380,316 | 1/1995 | Alta et al. . |
| 5,386,828 | 2/1995 | Owens et al. . |
| 5,389,096 | 2/1995 | Alta et al. . |
| 5,391,199 | 2/1995 | Ben-Haim . |
| 5,409,004 | 4/1995 | Sloan . |
| 5,409,019 | 4/1995 | Wilk . |
| 5,423,885 | 6/1995 | Williams . |
| 5,425,757 | 6/1995 | Tiefenbrun et al. . |
| 5,429,144 | 7/1995 | Wilk . |
| 5,441,516 | 8/1995 | Wang et al. . |
| 5,452,733 | 9/1995 | Sterman . |
| 5,453,090 | 9/1995 | Martinez et al. . |
| 5,458,615 | 10/1995 | Klemm . |
| 5,464,404 | 11/1995 | Abela et al. . |
| 5,464,650 | 11/1995 | Berg et al. . |
| 5,466,242 | 11/1995 | Mori . |
| 5,476,505 | 12/1995 | Limon . |
| 5,480,422 | 1/1996 | Ben-Halm . |
| 5,487,739 | 1/1996 | Aebischer et al. . |
| 5,514,176 | 5/1996 | Bosley, Jr. et al. . |
| 5,551,427 | 9/1996 | Altman . |
| 5,551,954 | 9/1996 | Buscemi et al. . |
| 5,558,091 | 9/1996 | Acker et al. . |
| 5,562,619 | 10/1996 | Mirarchi et al. . |
| 5,569,272 | 10/1996 | Reed . |
| 5,571,168 | 11/1996 | Toro . |
| 5,593,412 | 1/1997 | Martinez et al. . |
| 5,593,434 | 1/1997 | Williams . |
| 5,602,301 | 2/1997 | Field . |
| 5,614,206 | 3/1997 | Randolph et al. . |
| 5,643,308 | 7/1997 | Markman . |
| 5,653,756 | 8/1997 | Clarke et al. . |
| 5,655,548 | 8/1997 | Nelson . |
| 5,662,124 | 9/1997 | Wilk . |
| 5,676,850 | 10/1997 | Reed et al. . |
| 5,690,643 | 11/1997 | Wijay . |
| 5,735,897 | 4/1998 | Buirge . |
| 5,741,330 | 4/1998 | Brauker et al. . |
| 5,755,682 | 5/1998 | Knudson et al. . |
| 5,756,127 | 5/1998 | Grisoni et al. . |
| 5,769,843 | 6/1998 | Abela et al. . |
| 5,782,823 | 7/1998 | Mueller . |
| 5,785,702 | 7/1998 | Murphy et al. . |
| 5,792,453 | 8/1998 | Hammond et al. . |
| 5,797,870 | 8/1998 | March et al. . |
| 5,807,384 | 9/1998 | Mueller . |
| 5,810,836 | 11/1999 | Evans et al. . |
| 5,817,101 | 10/1998 | Fiedler . |
| 5,824,049 | 10/1998 | Ragheb et al. . |
| 5,824,071 | 10/1998 | Nelson et al. . |
| 5,827,304 | 10/1998 | Hart .................................... 606/194 |
| 5,830,502 | 11/1998 | Dong et al. . |
| 5,833,608 | 11/1998 | Acker . |
| 5,840,059 | 11/1998 | March et al. . |
| 5,861,032 | 1/1999 | Subramaniam . |
| 5,879,383 | 3/1999 | Bruchman et al. . |
| 5,899,915 | 5/1999 | Saadat . |
| 5,968,052 | 10/1999 | Sullivan, III et al. ............... 606/108 |
| 5,971,993 | 10/1999 | Hussein et al. ..................... 606/108 |
| 5,980,514 | 11/1999 | Kupiecki et al. . |
| 5,980,548 | 11/1999 | Evans et al. ........................ 606/185 |
| 6,045,565 | 4/2000 | Ellis et al. . |
| 6,051,001 | 4/2000 | Borghi ................................ 606/108 |

FOREIGN PATENT DOCUMENTS

| | | |
|---|---|---|
| 0 717 969A2 | 6/1996 | (EP) . |
| 0 732 089 A2 | 9/1996 | (EP) . |
| 0 207 438 | 1/1997 | (EP) . |
| 0 812 574 A2 | 12/1997 | (EP) . |
| 1278965 | 1/1961 | (FR) . |
| 1514319 | 1/1967 | (FR) . |
| 2 725 615 | 10/1994 | (FR) . |
| 2026640 C1 | 1/1995 | (RU) . |
| 2063179 C1 | 1/1995 | (RU) . |
| WO 89/01798 | 3/1989 | (WO) . |
| WO 91/15254 | 10/1991 | (WO) . |
| WO 94/05265 | 3/1994 | (WO) . |
| WO 97/32551 | 9/1997 | (WO) . |
| WO 97/44071 | 11/1997 | (WO) . |
| WO 97/47253 | 12/1997 | (WO) . |
| WO 98/08456 | 3/1998 | (WO) . |
| WO 98/1664 | 4/1998 | (WO) . |
| WO 98/2553 | 6/1998 | (WO) . |
| WO 98/32859 | 7/1998 | (WO) . |
| WO 98/46115 | 10/1998 | (WO) . |
| WO 98/05307 | 12/1998 | (WO) . |
| WO 99/38459 | 8/1999 | (WO) . |

OTHER PUBLICATIONS

A. Sachinopoulou et al., Invited Review Transmyocardial Revascularization, Lasers in Medical Science 1995, vol. 10, pp. 83–91, Sep. 1995.

B. Schumacher et al., Induction Neoangiogenesis in Ischemic Myocardium by Human Growth Factors, First Clinical Results of a New Treatment of Coronary Heart Disease, Clinical Investigation and Reports, pp. 645–650, Dec. 1997.

Charles T. Doiter, Transluminally–placed Coilspring Endarterial Tube Grafts, Long–term Patency in Canine Popliteal Artery, Investigative Radiology, pp. 329–332, Sep.–Oct. 1969.

C. Massimo, et al., Myocardial Revascularization By a New Method of Carrying Blood Directly from the Left Ventricular Cavity into the Coronary Circulation, Journals of Thoracic Surgery vol. 34, No. 2, 257–264, Aug. 1957.

Garrett Lee et al., Feasibility of Intravascular Laser Irradiation for In Vivo Visualization and Therapy of Cardiocirculatory Diseases, American Heart Journal, vol. 103 No. 6, pp. 1076–1077.

Garrett Lee et al., Laser–Dissolution of Coronary Atherosclerotic Obstruction, American Heart Journal, vol. 102, No. 6, part 1, pp. 1074–1075, Dec. 1981.

George S. Abela et al., Use of Laser Radiation to Recanalize Totally Obstructed Coronary Arteries (Abstract), Journal American College Cardiology 1983:1(2):691.

George S. Abela et al., Laser Revascularization: What Are Its Prospects?, Journal of Cardiovascular Medicine, pp. 977–984, Sep. 1983.

Isam N. Anabtawi et al., Experimental Evaluation of Myocardial Tunnelization as a Method of Myocardial Revascularization, Journal of Thoracic and Cardiovascular Surgery, vol. 58, No. 5, pp. 638–646, Nov. 1969.

John E. Hershey et al., Transmyocardial Puncture Revascularization, Geriatrics, pp. 101–108, Mar. 1969.

Ladislav Kuzela et al., Experimental Evaluation of Direct Transventricular Revascularization, Journal of Thoracic Cardiovascular Surgery, vol. 57, No. 6, pp. 770–773, Jun. 1969.

M. A. Martinelli, et al., Intraluminal Ultrasound Guidance of Transverse Laser Coronary Atherectomy, Optical Fibers in Medicine vol. 1201, pp. 68–78, (1990).

Mahmood Mirhoseini et al., Myocardial Revascularization by Laser: A Clinical Report; Lasers in Surgery and Medicine 3: 241–245 (1983).

Mahmood Mirhoseini et al., Revascularization of the Heart by Laser; Journal of Microsurgery, pp. 253–260, Jun. 1981.

Mahmood Mirhoseini et al., Transventricular Revascularization by Laser, Laser in Surgery and Medicine, vol. 2, pp. 187–198, 1982.

Mahmood Mirhoseini et al., Clincal Report: Laser Myocardial Revascularization, Lasers in Surgery and Medicine vol. 6, pp. 459–461, 1986.

Mahmood Mirhoseini et al., New Concepts in Revascularization of the Myocardium, The Annals of Thoracic Surgery, vol. 45, No. 4, pp. 415–420, Apr. 1988.

P. Walter et al., Treatment of Acute Myocardial Infarction by Transmural Blood Supply from the Ventricular Cavity, Department of Surgery and Department of Radiology of the Hannover Medical School, Hanover, pp. 130–138, (1971).

Peter Whittaker, et al., Transmural Channels Can Protect Ischemic Tissue, Assessment of Long–term Myocardial Response to Laser and Needle–Made Channels, Circulation, vol. 93, No. 1, pp. 143–152, Jan. 1996.

P.K. Sen, et al, Further Studies in Multiple Trasnmyocardial Acupuncture as a Method of Myocardial Revascularization, Surgery, vol. 64, No. 5, pp. 861–870, Nov. 1968.

P.K. Sen et al, Transmyocardial Acupuncture, A New Approach to Myocardial Revascularization; Journal of Thorocic and Cardiovascular Surgery, vol. 50, No. 2, pp. 181–189, Aug. 1965.

R.I. Hardy et al., Regional Myocardial Blood Flow and Cardiac Mechanics in Dog Hearts with $CO_2$ Laser–Induced Intramyocardial Revascularization, Basic Research Cardiology, 85:179–197 (1990).

Roque Pifarre et al., Myocardial Revascularization by Transmyocardial Acupuncture: A Physiologic Impossibility; Journal of Thoracic and Caridovascular Surgery; vol. 58, No. 3, pp. 424–429, Sep. 1969.

Valluvan Jeevanandam et 1., Myocardial Revascularization by Laser–Induced Channels, Surgical Forum Vo. IVL, American College of Surgeons 76th Clinical Congress, vol. 4, pp. 225–227, Oct. 1990.

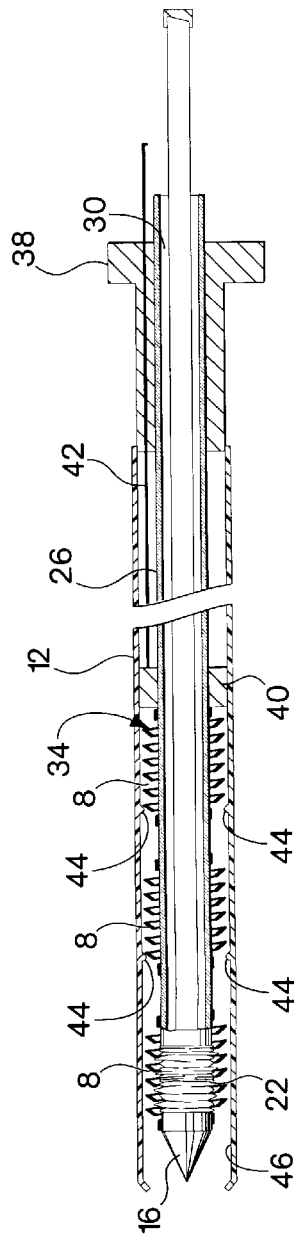
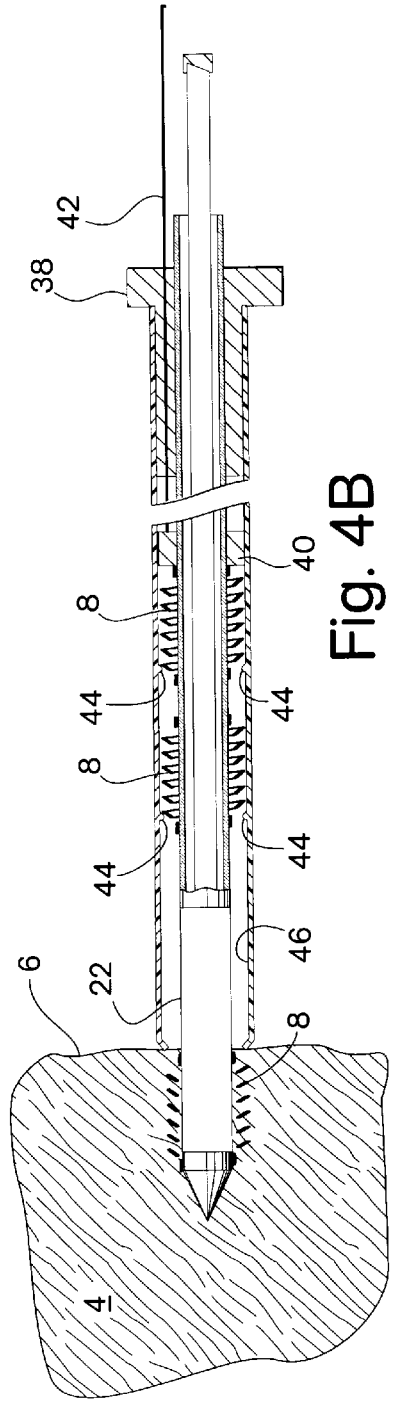
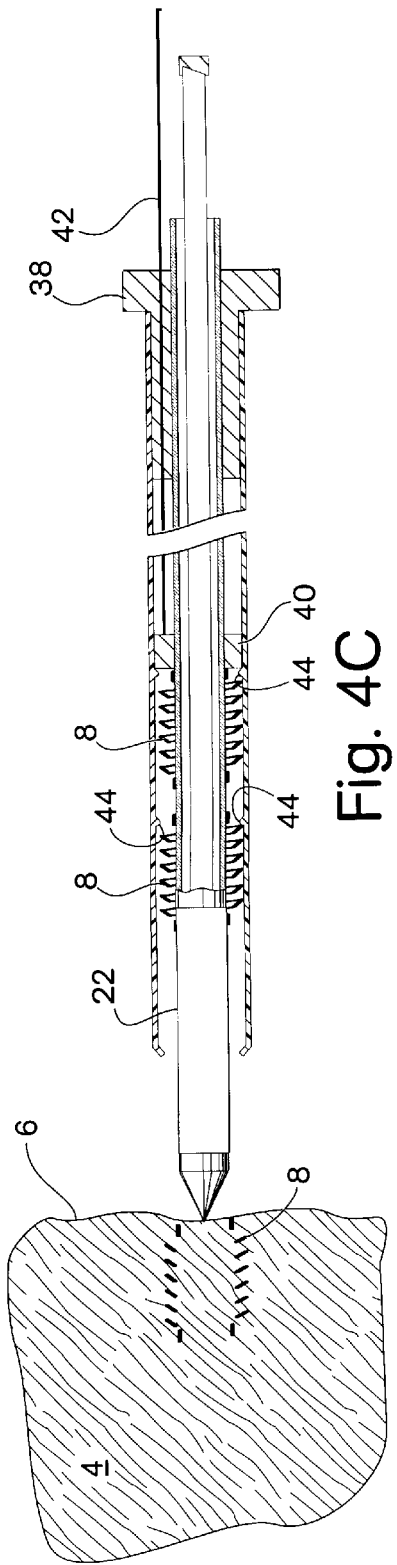

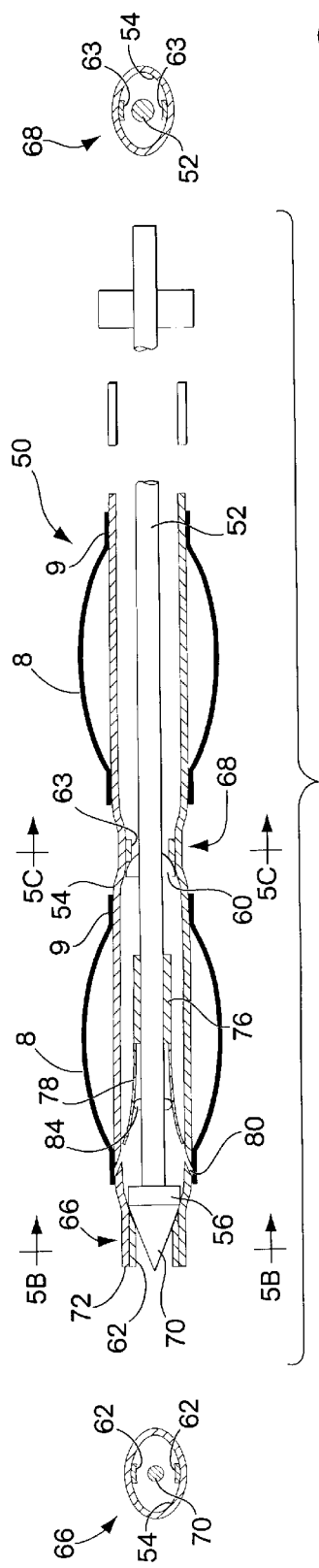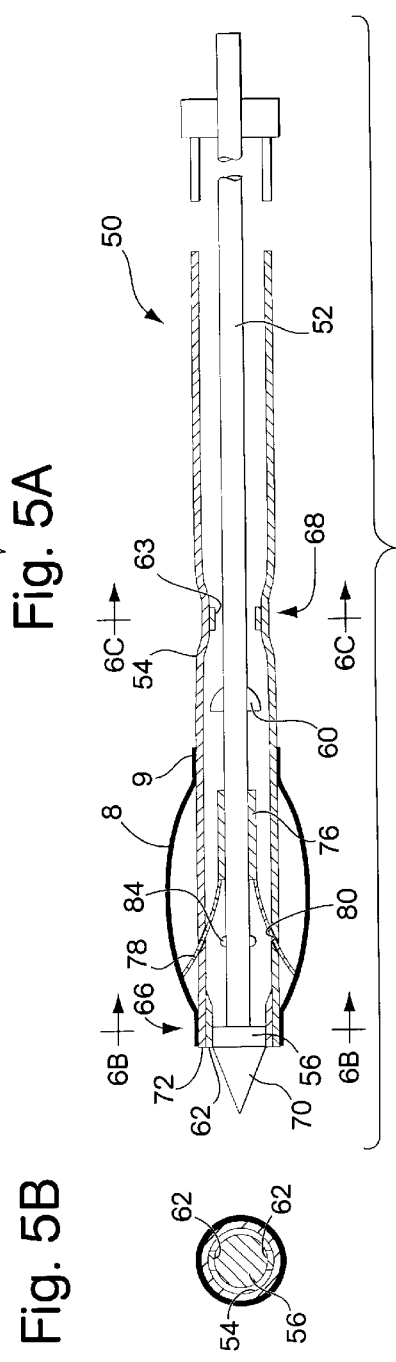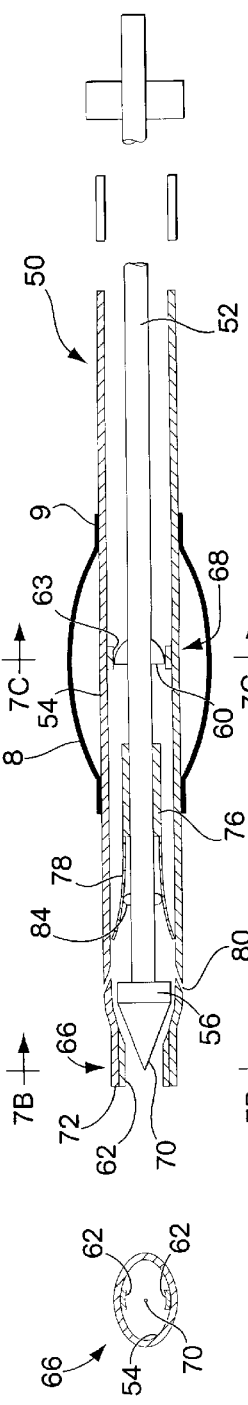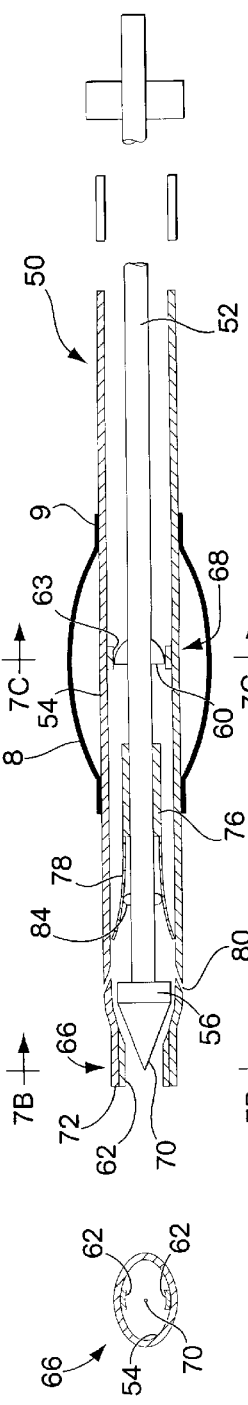

IMPLANT DELIVERY SYSTEM

FIELD OF THE INVENTION

This invention relates to delivery devices for implants placeable within tissue of the human body. Specifically, the invention relates to delivery of implants configured to aid in the restoration of blood flow to myocardial tissue of the heart. The invention includes a mechanism to monitor the position of the device and deliver drugs.

BACKGROUND OF THE INVENTION

Tissue becomes ischemic when it is deprived of adequate blood flow. Ischemia causes pain in the area of the affected tissue and, in the case of muscle tissue, can interrupt muscular function. Left untreated, ischemic tissue can become infarcted and permanently non-functioning. Ischemia can be caused by a blockage in the vascular system that prohibits oxygenated blood from reaching the affected tissue area. However, ischemic tissue can be revived to function normally despite the deprivation of oxygenated blood because ischemic tissue can remain in a hibernating state, preserving its viability for some time. Restoring blood flow to the ischemic region serves to revive the ischemic tissue.

Although ischemia can occur in various regions of the body, often tissue of the heart, the myocardium, is affected by ischemia due to coronary artery disease, occlusion of the coronary artery, which otherwise provides blood to the myocardium. Muscle tissue affected by ischemia can cause pain to the individual affected. Ischemia can be treated, if a tissue has remained viable despite the deprivation of oxygenated blood, by restoring blood flow to the affected tissue.

Treatment of myocardial ischemia has been addressed by several techniques designed to restore blood supply to the affected region. Coronary artery bypass grafting CABG involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2, August 1965, pp. 181–189. Although others have reported varying degrees of success with various methods of piercing the myocardium to restore blood flow to the muscle, many have faced common problems such as closure of the created channels. Various techniques of perforating the muscle tissue to avoid closure have been reported by researchers. These techniques include piercing with a solid sharp tip wire, hypodermic tube and physically stretching the channel after its formation. Reportedly, many of these methods still produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularization of the Heart by Laser", *Journal of Microsurgery*, Vol. 2, No. 4, June 1981, pp. 253–260. The laser was said to form channels in the tissue that were clean and made without tearing and trauma, suggesting that scarring does not occur and the channels are less likely to experience the closure that results from healing. U.S. Pat. No. 5,769,843 (Abela et al.) discloses creating laser-made TMR channels utilizing a catheter based system. Abela also discloses a magnetic navigation system to guide the catheter to the desired position within the heart. Aita U.S. Pat. Nos. 5,380,316 and 5,389,096 disclose another approach to a catheter based system for TMR.

Although there has been some published recognition of the desirability of performing transmyocardial revascularization (TMR) in a non-laser catheterization procedure, there does not appear to be evidence that such procedures have been put into practice. For example, U.S. Pat. No. 5,429,144 Wilk discloses inserting an expandable implant within a preformed channel created within the myocardium for the purposes of creating blood flow into the tissue from the left ventricle.

Performing TMR by placing stents in the myocardium is also disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open channel in the myocardium through which blood enters from the ventricle and perfuses into the myocardium.

Angiogenesis, the growth of new blood vessels in tissue, has been the subject of increased study in recent years. Such blood vessel growth to provide new supplies of oxygenated blood to a region of tissue has the potential to remedy a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation*, 1998; 97:645–650. The authors noted that such treatment could be an approach to management of diffused coronary heart disease after alternative methods of administration have been developed.

SUMMARY OF THE INVENTION

The present invention provides a delivery system for placing implants within tissue in the human body. The implant delivery system of the present invention provides several novel features, which are useful in delivering implants into tissue.

In one aspect of the invention a delivery device is provided that is especially configured to carry multiple tubular shaped implants at its distal end, engaging the implants by their inside surfaces. The delivery devices are inserted percutaneously into a patient and navigated to the site where the implant is to be located. The delivery systems of the present invention are particularly well suited for delivering implants into the myocardium to perform transmyocardial revascularization (TMR). Implants such as stents may be placed by the delivery device into the myocardial tissue to a proper depth to encourage revascularization of ischemic tissue. In such a procedure, positioning the implants into the proper depth within the myocardium is important to the success of the procedure because it has been observed that areas of the myocardium closer to the endocardial surface and to the epicardial surface are more likely to be responsive to revascularization. Additionally, spacing of the implants relative to one another in an area of ischemic tissue is important to the success of the revascularization process and avoiding undesirable side effects of placing foreign objects in the muscle tissue of the myocardium. Additionally, it may be desirable to deliver a therapeutic substance to the implant location, before, after or during delivery of the implant to promote revascularization activity such as angiogenesis. The features of the present invention address these concerns as will be discussed in greater detail below.

Reaching the intended implant delivery location with the delivery devices of the present invention first requires placement of a guide catheter prior to navigation of a deliverable catheter into the left ventricle. A steerable catheter that is placeable within the left ventricle and positionable in multiple locations with one catheterization is disclosed in U.S. application Ser. No. 09/073,118 filed May 5, 1998, the entirety of which is herein incorporated by reference. The delivery devices as described herein are insertable through the lumen of the delivery catheter and are extendible past its distal end to place the implants within the myocardial tissue. The delivery catheter provides directional control so that the delivery devices of the present invention can deliver multiple implants to a variety of locations within a given area of ischemic tissue.

In one embodiment of a delivery device of the present invention the device comprises a catheter having a compressible sleeve at its distal end which forms into a plurality of random folds when it is compressed, expanding its diameter and serving to capture the inside surface of any tubular object placed over it. The crinkle tube may be formed from a polymer such as polyethylene terethalate (PET). The crinkle tube can securely retain tubular implants over its crinkled, radially expanded surface to a sufficient degree such that delivery into tissue does not push the implant off of the delivery device. Additionally, the crinkle tube catheter may be used in conjunction with an outer catheter shaft having a plurality of interior projections which engage a plurality of implants in cue while the crinkle tube shaft delivers the implants from the distal end of the catheter sequentially.

In another embodiment, a tubular implant is maintained on the catheter behind an oval shaped segment of the catheter which presents a larger profile than the inside diameter of the tubular implant. A member slidable within the catheter engages the oval portion to deform it into a round shape, thereby permitting the implant to slip off the distal end of the shaft. Simultaneously with deformation of the oval to a circle shape, the inner member causes arms to protrude from the interior of the catheter and to engage the implant and push it in a distal direction so that it becomes implanted in the tissue. Additionally, the catheter has the ability to carry multiple implants over its shaft. The implants waiting in cue are also maintained in position on the shaft by a oval shape segment of the shaft that can be deformed to a circular shape thereby permitting advancement of the next implant.

In yet another embodiment of the delivery system, the delivery catheter comprises an elongate shaft that contains pressurized fluid within its lumen to motivate a plunger located at the distal end of the shaft and attached to a single implant attachment device. When fluid within the lumen of the delivery catheter is pressurized, the plunger moves from its position against proximal stops distally to its position against distal stops. That length of travel is sufficient to push the implant attached to the plunger into the intended tissue location. The benefit of the fluid pressure delivery system is a reduction in moving components needed to cause distal movement of the implant at the distal end of the catheter from the proximal end of the catheter which is manipulated outside of the patient.

Another feature of the present invention includes a dual bladder drug delivery system which may be associated with the delivery catheters discussed above. The dual bladder arrangement provides a first bladder which contains a therapeutic substance near the distal end of the delivery catheter and a second bladder arranged near the first bladder so as to impinge upon the space of the first bladder when the second bladder is inflated. The second bladder is inflated with an inexpensive fluid simply to cause the evacuation of the first bladder, which contains a therapeutic substance to be delivered. The first bladder may be provided with a series of perfusion ports through which the therapeutic substance can be forced through when pressurized by the reducing volume imposed by the inflation of the second bladder. The benefit of the system is to avoid the waste of expensive therapeutic substances by filling an entire full length lumen with the substance in order to force it from the distal end of a delivery catheter. With the dual bladder delivery system, an inexpensive fluid can be used to occupy the space along the full length of the delivery catheter, yet its pressurization force can be applied to deliver a small quantity of the therapeutic substance maintained only at the distal end of the catheter.

Another feature of the present invention is a depth monitor, which may be applied to any of the above delivery catheters. The depth monitor uses changes in pressure being measured at the distal end of the catheter to signal the operator that the distal end of the catheter has been placed within myocardial tissue to a certain depth sufficient to implant the device. This depth monitoring is accomplished by providing one or a plurality of pressure ports at the distal end of the catheter that will be inserted into tissue in order to deliver the implant that it carries. The pressure port(s) are spaced a known distance from the distal end of the delivery catheter. The interior lumen of the catheter can transmit the pressure experienced at the distal end of the catheter through individual lumens to the proximal end where a pressure monitoring device for each pressure port is attached to the proximal end of the delivery device. When the distal end of the delivery catheter is in the left ventricle, pressure readings at the distal end will be dynamic. However, after the distal end of the delivery catheter enters the tissue to implant the device, the pressure ports become covered with surrounding tissue resulting in dampened or static signal. The most proximal pressure port when covered by the surrounding tissue, will likewise transmit a dampened signal and signals the operator that the distal end of the delivery catheter has been placed to a sufficient depth within the tissue to deliver the implant.

Another feature of the present invention is a navigation system utilizing magnetic fields transmitted over the body to identify the location within a patient of a catheter having sensing electrodes that interact with the electromagnetic coils. Computer software processes the information obtained from the magnetic pick-up coils and places the catheter on a virtual image of the heart to give the operator a general idea of where the catheter is located and what areas of ischemic tissue have been treated with implant devices. Because the delivery devices of the present invention are capable of delivering more than one implant to an area of ischemic tissue with one catheterization, a navigation system helping to guide the placement of the delivery catheter and implants is helpful.

It is an object of the present invention to provide an implant delivery system that is simple and effective to use.

It is yet another object of the present invention to provide an implant delivery system that is suitable for varying implant devices to the myocardium of the heart that will aid in revascularization of ischemic tissue.

It is yet another object of the invention to provide an implant delivery device that operates to grasp a tubular shaped implant by its inside surface so that the implant may be inserted into tissue.

It is another object of the invention to provide an implant delivery device that utilizes fluid pressure through the delivery catheter to insert the implant into the subject tissue.

It is yet another object of the invention to provide an implant delivery device that includes a dual bladder drug delivery system that reduces waste of expensive therapeutic substances in their application to a treatment site through a catheter.

It is still another object of the invention to provide a depth monitor capable of being associated with a delivery device that utilizes pressure sensed at the distal end of the catheter to reliably determine the location of the distal end of the device.

It is yet another object of the invention to provide a navigation system that is capable of identifying the location of a catheter delivering mechanical TMR inducing devices, within the human heart so that the catheter can be moved to various locations delivering multiple devices with one insertion into the heart.

BRIEF DESCRIPTION OF THE DRAWINGS

The foregoing and other objects and advantages of the invention will be appreciated more fully from the following further description thereof, with reference to the accompanying diagrammatic drawings wherein:

FIGS. 4A–4C are partial sectional illustrations of a multiple implant device;

FIG. 5A is a partial sectional view of a oval tube delivery device;

FIG. 5B is a sectional view taken along the line 5B—5B of FIG. 5A;

FIG. 5C is a sectional view taken along the line 5C—5C of FIG. 5A;

FIG. 6A is a partial sectional view of an oval tube delivery device;

FIG. 6B is a sectional view taken along the line 6B—6B of FIG. 6A;

FIG. 6C is a sectional view taken along the line 6C—6C of FIG. 6A;

FIG. 7A is a partial sectional view of an oval tube delivery device;

FIG. 7B is a sectional view taken along the line 7B—7B of FIG. 7A;

FIG. 7C is a sectional view taken along the line 7C—7C of FIG. 7A;

DESCRIPTION OF THE ILLUSTRATIVE EMBODIMENTS

Figure 1:
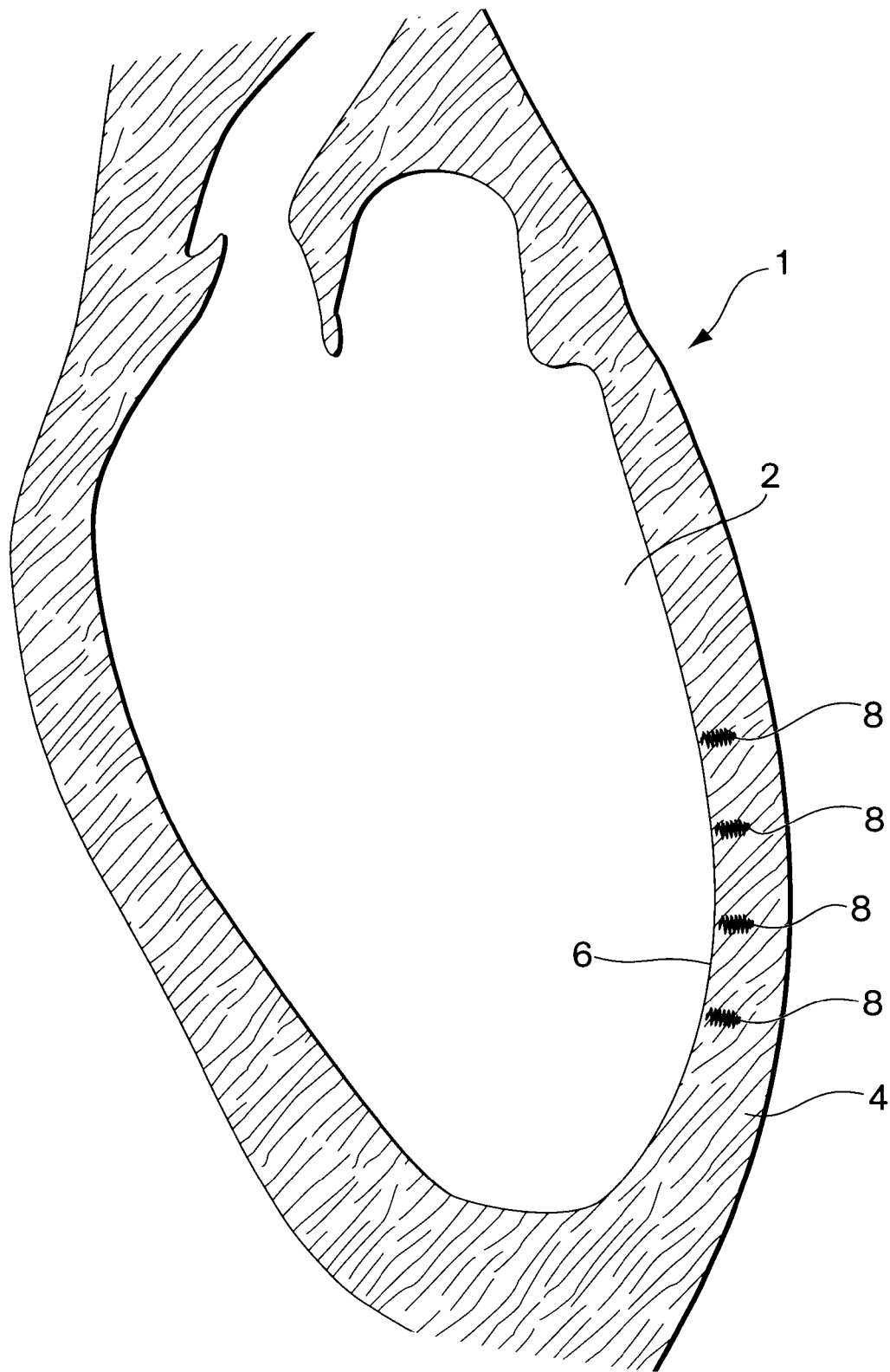
FIG. 1 shows a sectional illustration of the left ventricle of a human heart.
Figure 2A:
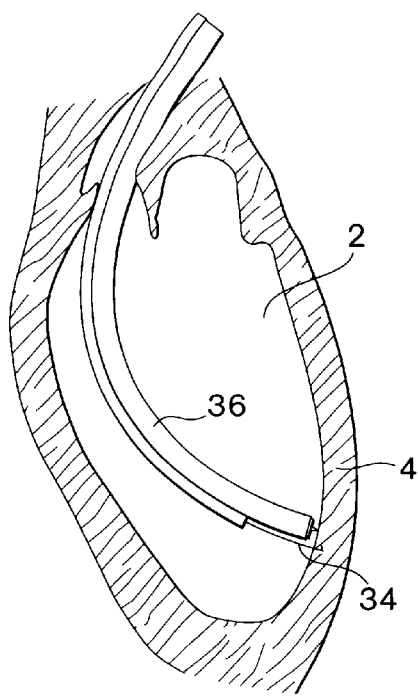
FIGS. 2A–2D illustrate the steps of percutaneously delivering an implant to an area of the myocardium.
Figure 2B:
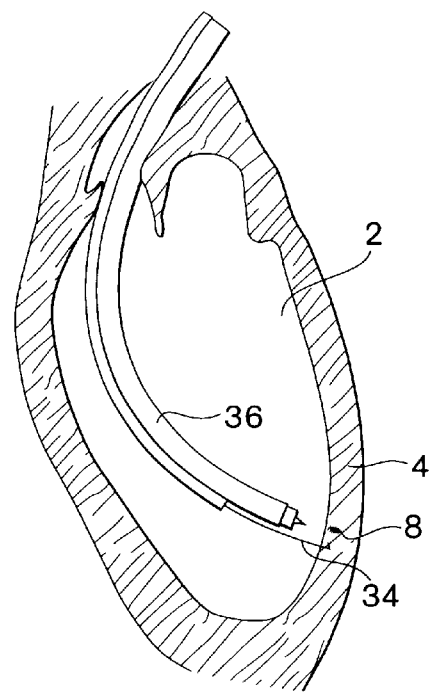
Figure 2C:
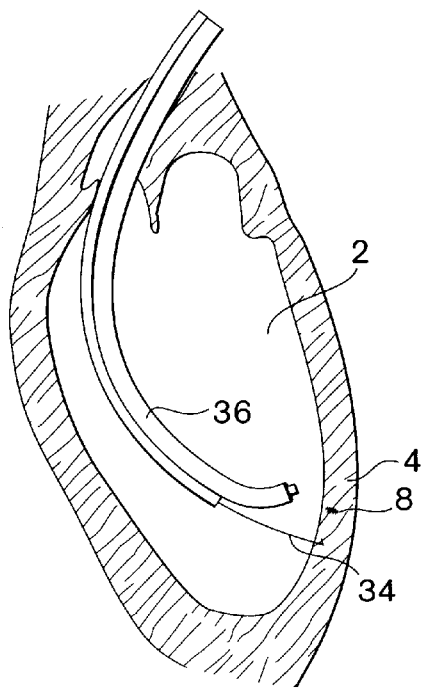
Figure 2D:
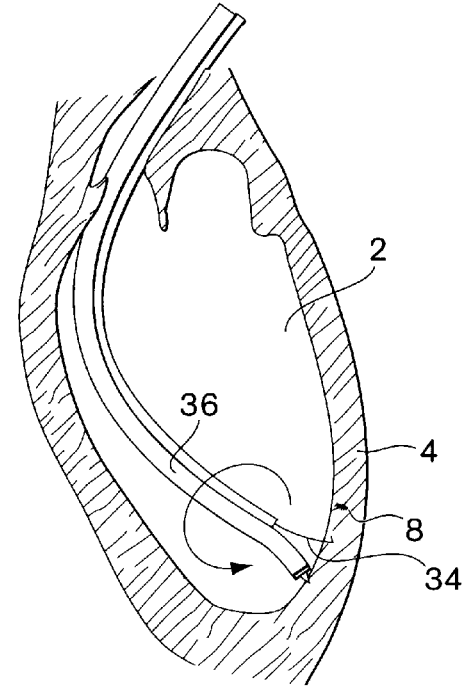

FIG. 1 shows a sectional illustration of the left ventricle 2 of a human heart 1. Several implants 8 are placed within the myocardium 4 adjacent the endocardial surface 6. As shown in FIGS. 2A–2D, access to the endocardial surface 6 of the myocardium 8 is gained through a steerable delivery catheter 36 inserted into the left ventricle 2. It is through the delivery catheter 36 that the delivery devices of the present invention are inserted to carry the individual implants 8 into the myocardial tissue. It is noted, throughout the description of the delivery devices and their associated methods, "proximal" refers to the direction along the delivery path leading external of the patient and "distal" refers to the direction leading internal to the patient.

To access the left ventricle of the heart percutaneously, a guide catheter (not shown) may be navigated through the patient's vessels to reach the left ventricle 2 of the heart 1. A barbed tip guidewire 34 may then be inserted through the guide catheter and into the ventricle where it pierces the myocardium 4 and becomes anchored within the tissue. After anchoring the guidewire, the steerable delivery catheter 36 may be advanced over the guidewire to become positioned within the ventricle in close proximity to the endocardium to facilitate delivery of implants. To facilitate delivery of multiple implants, the guidewire lumen of the delivery catheter 36 may be eccentrically located on the catheter. Therefore, when the catheter is rotated about the guidewire, the center of the catheter will rotate through a circular path as demonstrated in FIGS. 2C and 2D, to encompass a broader delivery area with only a single guidewire placement. The outside diameter of the delivery catheter is preferably less than 0.100 inch. Additionally, the delivery catheter may be provided with steering capability by means of a pull wire extending the length of the catheter and attached at its distal end such that pulling on the wire from the proximal end causes the distal tip of the catheter to be deflected. Therefore, the steering capability provides a broader range of delivery area with a single catheterization. A detailed description of the construction of a delivery catheter for reaching multiple sites within the left ventricle is described in U.S. patent application Ser. No. 09/073,118 filed May 5, 1998, the entire disclosure of which is herein incorporated by reference.

Figure 3A:
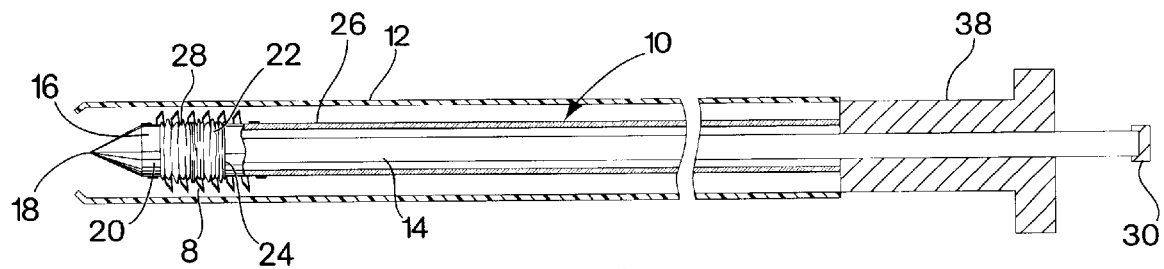
FIG. 3A is a partial sectional illustrational of the crinkle tube delivery device.
Figure 3B:
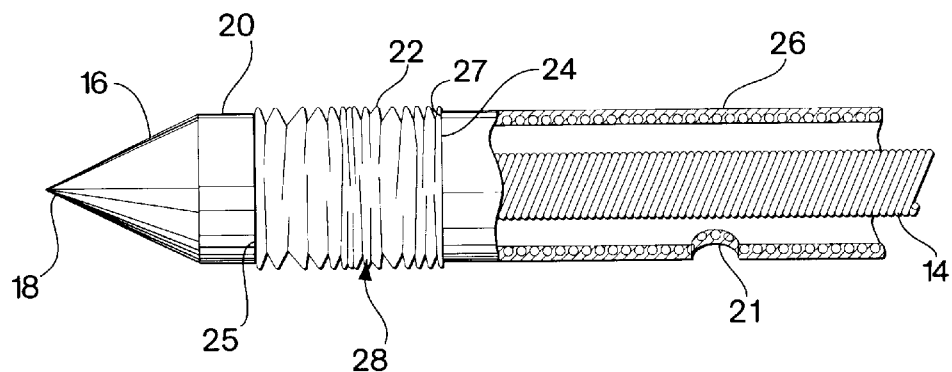
FIG. 3B is a detail of the crinkle tube in compression.
Figure 3C:
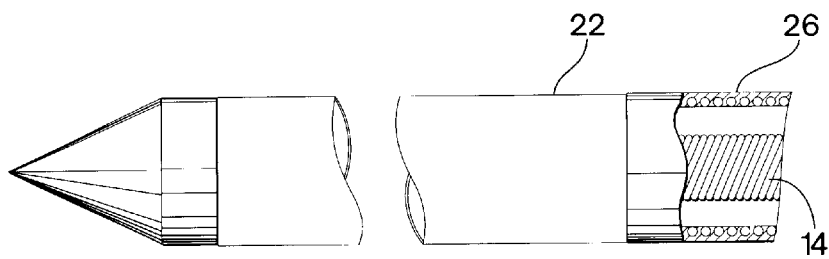
FIG. 3C is a detail of the crinkle tube in tension.
Figure 3D:
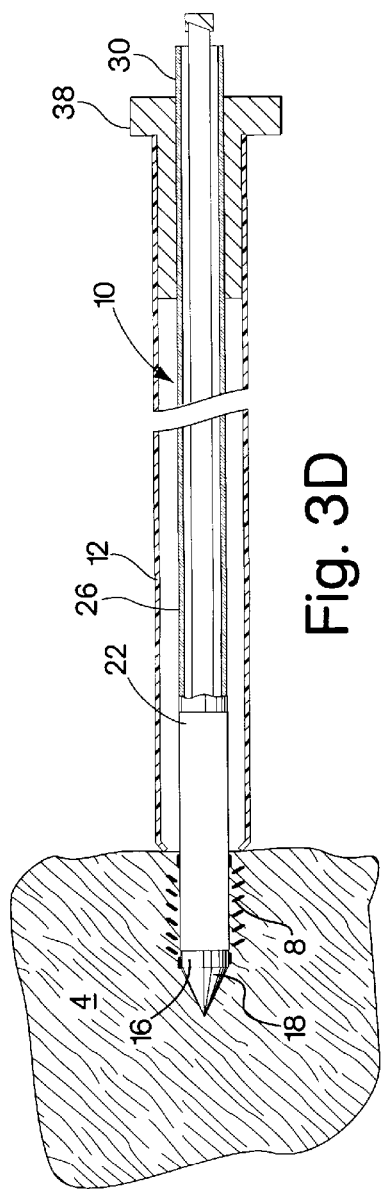
FIG. 3D is a partial sectional illustration of the crinkle tube device delivering an implant.
Figure 3E:
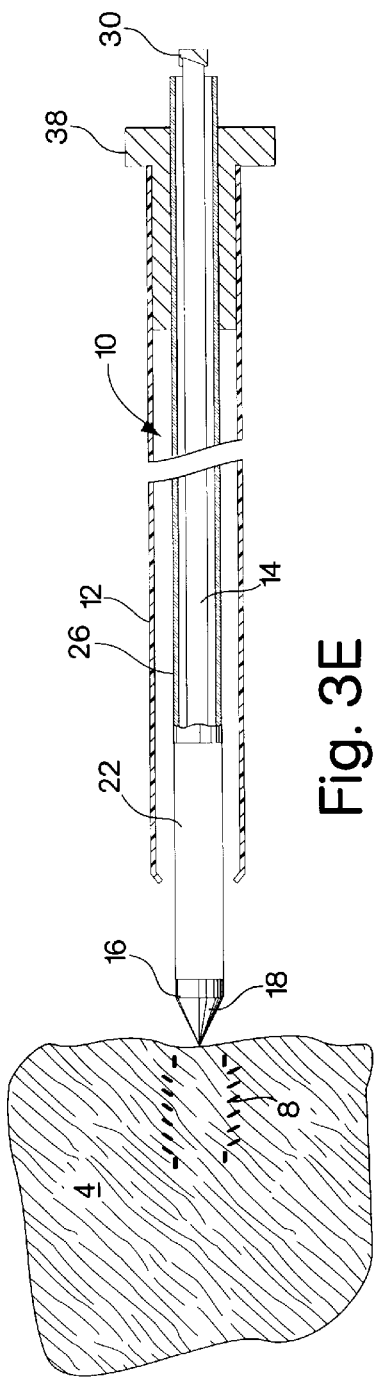
FIG. 3E is a partial sectional illustration of the crinkle tube device being withdrawn from the implant location.

FIG. 3A shows a partial cut-away view of a preferred delivery device 10 for the TMR implants 8. The delivery device 10 shown in FIG. 3A may be used with a guide catheter 12 rather than the steerable catheter 36 discussed above. A delivery device 10 comprises an elongate solid shaft or core wire 14 having a sharp obturator head 16 at its distal end. The obturator head 16 is formed at the distal end of the core wire 14 by any convenient means of building a mass at the end of a core wire. For example, several thin and small sleeves and springs may be amassed at the distal end and melted together to form a bulbous tip which is later ground to form a sharp, piercing tip 18. Included within the mass of melted materials that form the distal obturator head 16, should be a radiopaque material such as gold or platinum to make the distal area of the device visible under fluoroscopy. Heat bonded to the proximal end 20 of the obturator head 16 is a flexible crinkle tube 22, shown in detail in FIG. 3B, formed from polyethylene terephthalate (PET). Attached to the proximal end 24 of the crinkle tube 22 by heat bonding is push tube 26 which is formed from a closely wound spring having a PET shrink tube formed around its outer surface filing in the voids created by the coils. The crinkle tube 22 collapses under compressive load to form a random pattern of folds 28, which serve to increase the overall diameter of the crinkle tube such that it comes into frictional contact with the inside diameter of a hollow or generally tubular implant 8 that is placed over it. When placed in tension as shown in FIG. 3C, the crinkle tube elongates and returns to a low diameter configuration without folds. The configuration of the crinkle tube is manipulated by relative movement of the core wire 14 having its obturator 16 joined to the distal end 25 of the crinkle tube relative to the push tube 26, which is joined to the proximal end of the crinkle tube 24. The shaft 14 and push tube 26 are slidable relative to each other and controllable from the proximal end of the device by a handle 38 and core wire extension 30. Movement of the handle and push tube in a distal direction and movement of the core wire and its extension in the proximal direction compress the crinkle tube 22 to capture the interior of an implant 8 for delivery into tissue as shown in FIG. 3A. It is this large diameter, crinkled configuration that the delivery device must maintain to restrain the implant during delivery into tissue. As shown in FIGS. 3C, 3D and 3E after delivery into tissue, the crinkle tube may be placed in tension, to withdraw the plurality of folds that engage the interior of the implant 8. With the crinkle tube 22 placed in a low profile configuration, the core wire extension 30 is advanced distally within the handle 38 and handle 38 advanced distally into the associated guide catheter 12 as shown in FIG. 3D. After reducing the profile of the crinkle tube 22 the implant easily slides off of the crinkle tube 22 over the obturator 16 as the device is withdrawn from the tissue as shown in FIG. 3E.

Figure 3F:
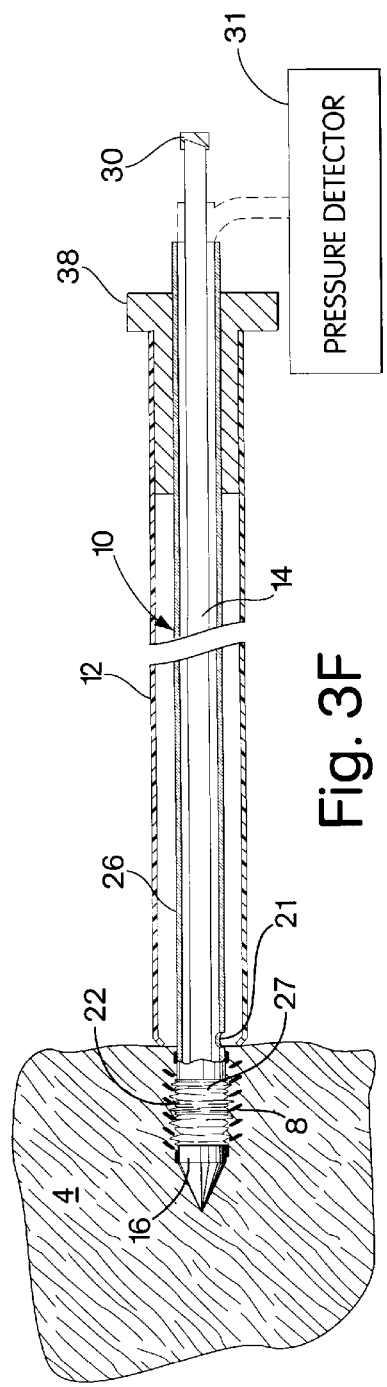
FIG. 3F is a partial sectional illustration of a delivery device having a depth monitor.

An alternative embodiment of the crinkle tube delivery device may be additionally equipped with a pressure dependent depth monitor. The depth monitor may be comprised of at least one pressure port 21, shown in FIGS. 3B and 3F, formed in the push tube 26 adjacent its distal end 27 and location of the crinkle tube 22 and implant. Pressure sensed through the port 21 is transmitted through the lumen defined by the push tube and is detected by a pressure detector 31 joined to the handle 38. Readings from the pressure detector may be shown on a hydraulic gauge or electronic readout.

The location of the pressure port 21 is a significant factor in interpreting the pressure information for proper implant delivery. When the pressure port is open to the left ventricle, pressure readings are dynamic. However, when the pressure port 21 is submerged and covered by tissue, pressure readings drop or become static. With placement of the pressure port just proximal of the implant mounting location on the push tube, a significant pressure dampening during delivery of an implant will signal the operator that, not only has the pressure port become embedded in the tissue, but also the implant, located distal to the pressure port, has become sufficiently imbedded in the tissue. Thus the implant can be released from the delivery device and into the tissue. Multiple pressure ports spaced along the distal end of the delivery device can provide an indicator of how deep the delivery device is in the tissue because at each successive port pressure can be monitored through individual lumens extending through the push tube and in communication with the pressure monitoring device 31.

FIG. 4A shows a variation of the crinkle tube delivery device, which is configured to sequentially deliver several preloaded implants 8. The multiple implant delivery device 34 operates much the same way as the single implant delivery device described above. The crinkle tube 22 grips the most distal implant 8 only, while the other implants wait in cue within the guide catheter 12 and over the push tube 26. The additional implants are restrained in their relative positions behind the most distal implant by resilient fingers 44 which project inwardly from the interior wall 46 of guide catheter 12. After the most distal implant is urged out of the guide catheter by the distal movement of the core wire and push shaft, as shown in FIG. 4B, the core wire and push shaft may be retracted back into the guide catheter as the remaining implants are indexed distally by the sliding distal movement of index cue 40 which may be manually slidable within the guide catheter 12 by indexing shaft 42. As the core wire 14 and push tube 26 are withdrawn proximally back into the guide catheter, the area of the crinkle tube 22 resides in the interior of the newly placed most distal implant. The push tube and core wire are again moved relative to each other to cause compression along the crinkle tube 22 so that the folds 28 of the crinkle tube 22 contact the interior surface of the next implant 8 to be delivered. The next implant to be delivered is preferably placed in a different location, spaced apart from the first implant by movement of the guide catheter 12 to a new area.

FIGS. 5A–C show another embodiment of the implant delivery device 50. The device operates to maintain an implant 8 over its outer shaft 54 by having a distal oval area 66 where the shaft defines an oval cross-sectional shape, as shown in FIG. 5B, where the largest diameter is larger than the inner diameter of the tubular implant 8, thereby preventing the implant from sliding off the end of the outer shaft 54. Additionally, a proximal oval cross-sectional shape area 68 in the outer shaft 54 maintains the implant 8 that is second in line in its mounted configuration on the catheter shaft. The natural tendency of the shaft 54 to maintain an oval shape at these areas serves to lock the implants 8 in place on the shaft as is shown in FIG. 5A. It is in this locked configuration that the most distal implant is navigated to the myocardium. The oval areas of the outer shaft 54 lock the implants in place so that they do not move as they are navigated to the tissue location.

FIGS. 6A–C show an implant 8 being delivered from the oval shaft embodiment 50. Once the delivery device is adjacent to the tissue to be penetrated, an inner shaft 52 is advanced distally causing a sharpened distal tip 70 of the shaft to emerge from the distal end 72 of the delivery device. The sharpened distal tip 70 pierces tissue as it is advanced in a distal direction to facilitate insertion of the implant 8 into a tissue. Also with the distal movement of the shaft 52, the distal cam 56 moves into engagement with distal shims 62, thereby causing the naturally oval area 66 to be elastically deformed into a round cross-sectional shape as is shown in FIG. 6B. The round configuration of the outer shaft 54 in this area permits the round implant to slide off the distal end 72 of the device. Further distal movement of the shaft 52 causes distal movement of a split tube 76, which is engaged by a proximal cam 60 joined to the shaft 52. Vanes 78 of the split tube move distally and curve radially outward through radial passages 80 formed into the sidewall of the outer shaft 54 to engage the interior of the most distal implant. The natural curvature of the vanes and the presence of biasing member 84 underneath the vanes urge them in a radially outward direction so that as they are moved distally within the shaft 54 the vanes are urged out of the radial passages 80 that are formed in the tube that comprises the outer shaft 54. Though the vanes serve to push the implant into the desired tissue location, their radial extent from the catheter shaft 54 could potentially interfere with the passage of the proximal end 9 of implant over the vanes. Therefore, to ensure that the implants are not hindered as they are pushed off the catheter shaft, the implants used with the present embodiment of delivery device should be configured to have a proximal opening that is larger than the distal opening and as large as the maximum extent of the natural radial extent of the vanes.

During delivery into the myocardium the proximal oval area 68 is maintained in the oval configuration to lock in place on the shaft 52 the implants 8 that are in cue to be delivered. However, after delivery of an implant into tissue, the shaft 52 is retracted proximally within the shaft 54 to shield the sharp distal tip 70 from tissue during movement of the shaft to the next location, as shown in FIG. 7A. Proximal movement of the shaft 52 also causes the proximal cam 60 to engage the proximal shim 63 located on the inner surface of the outer shaft lumen directly adjacent the proximal oval area 68, which forces the shaft to become circular temporarily in that area, as shown in FIG. 7C. Thus the secondary implants become free to cue forward, the next implant 8 moving up to be the next delivered. The arrangement of cams on the shaft dictates that when the proximal oval area 68 is deformed to be round, the distal oval area 66 remains in its undeformed oval configuration to prevent continued distal movement of implants 8 on the shaft 54 until they are ready to be delivered into tissue.

Figure 8:
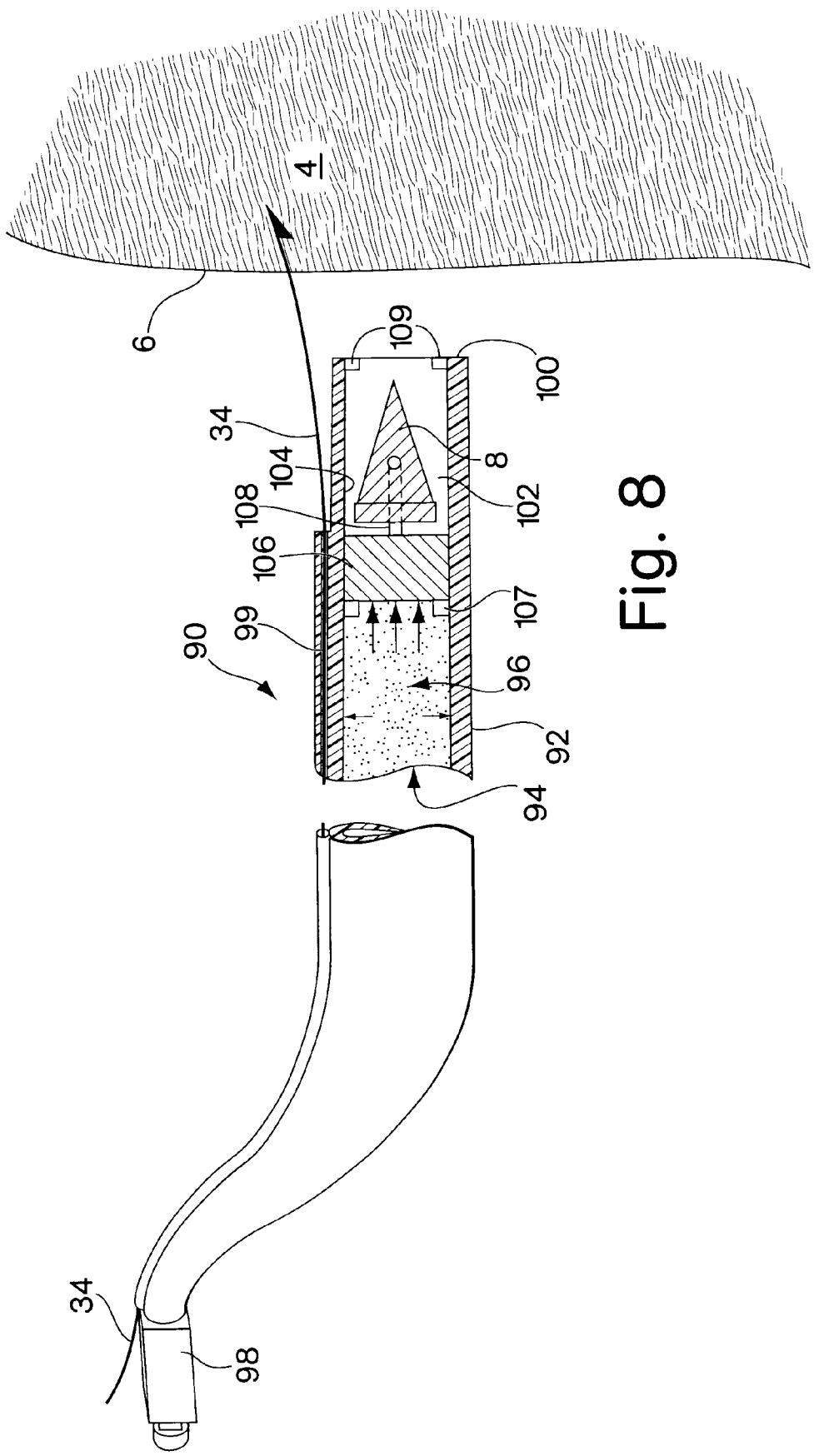
FIG. 8 is a sectional view of a pressurized fluid delivery device.

FIG. 8 is a partial sectional view of another embodiment of the delivery device of the present invention that uses pressurized fluid to provide the implantation force needed to insert a self-piercing stent into myocardial tissue. The fluid pressure delivery device 90 comprises an elongate shaft 92 having at least one lumen 94, which carries the pressurized fluid 96 such as water or saline. The fluid and a pressurization source are joined to the lumen at proximal luer fitting 98. The shaft may have a guidewire lumen 99 containing a barbed tip guidewire 34, as with the delivery catheter 36 described above. The barbed tip guidewire implanted within adjacent tissue helps provide leverage to resist movement of the distal tip 100 of the catheter when substantial fluid force is being applied to the tissue surface by the entering implant 8.

The distal portion 102 of the lumen 94 is configured as a track 104 to receive a slidable plunger 106 that forms a fluid tight seal with the track. Fluid pressure within the lumen 94 creates a force against the plunger causing it to slide distally. The plunger has joined to its distal face a catch member 108 that is configured to be releasably engagable with the interior of an implant 8 with which the device is intended to deliver into tissue. The extent of travel of the plunger within the track 104 is limited by proximal stops 107 and distal stops 109 that engage the plunger to limit its movement so that it does not become disassociated from the shaft lumen 94 when travel is maximized. To avoid the necessity of attaching a piercing member to the plunger, self-piercing implants are preferred for use with the present embodiment, such as shown in FIG. 8. Examples of self piercing implants intended for placement in the myocardium are described in U.S. patent application Ser. No. 09/073,118, filed May 5, 1998.

Figure 9A:
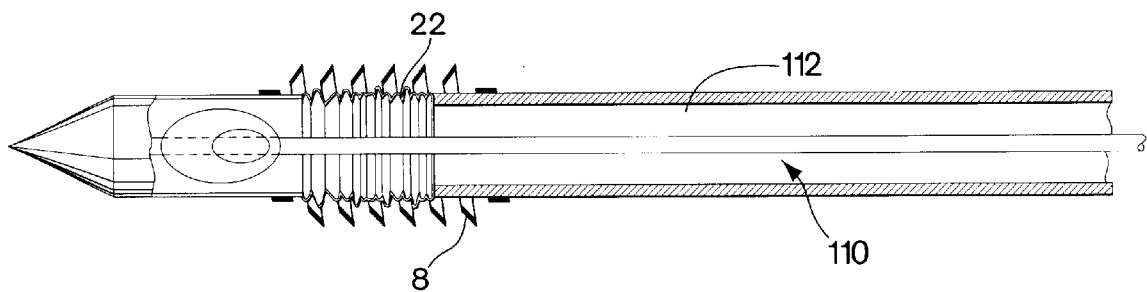
FIG. 9A is a sectional view of a double bladder therapeutic substance delivery device.
Figure 9B:
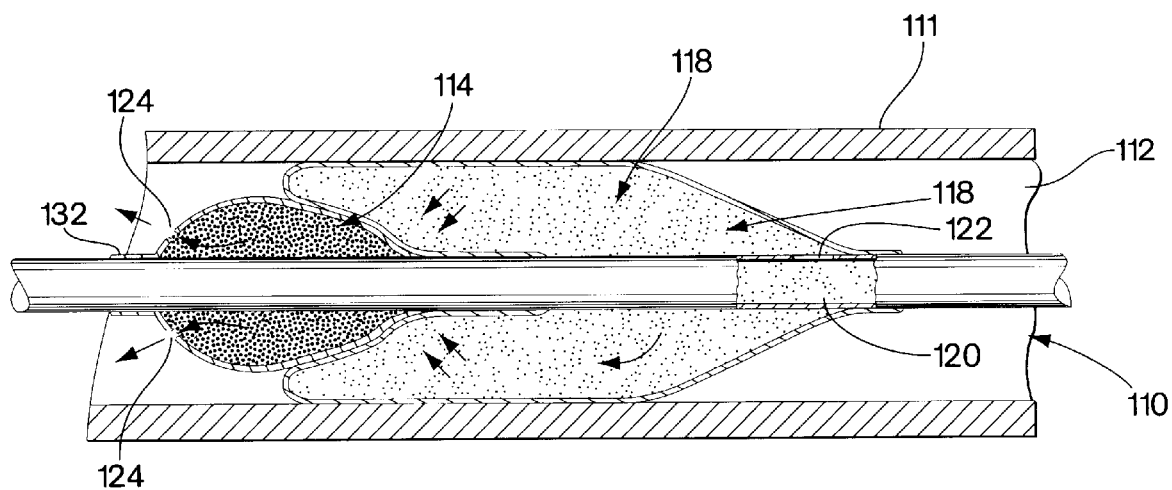
FIGS. 9B–9C are sectional views of the double bladder therapeutic substance delivery device.
Figure 9C:
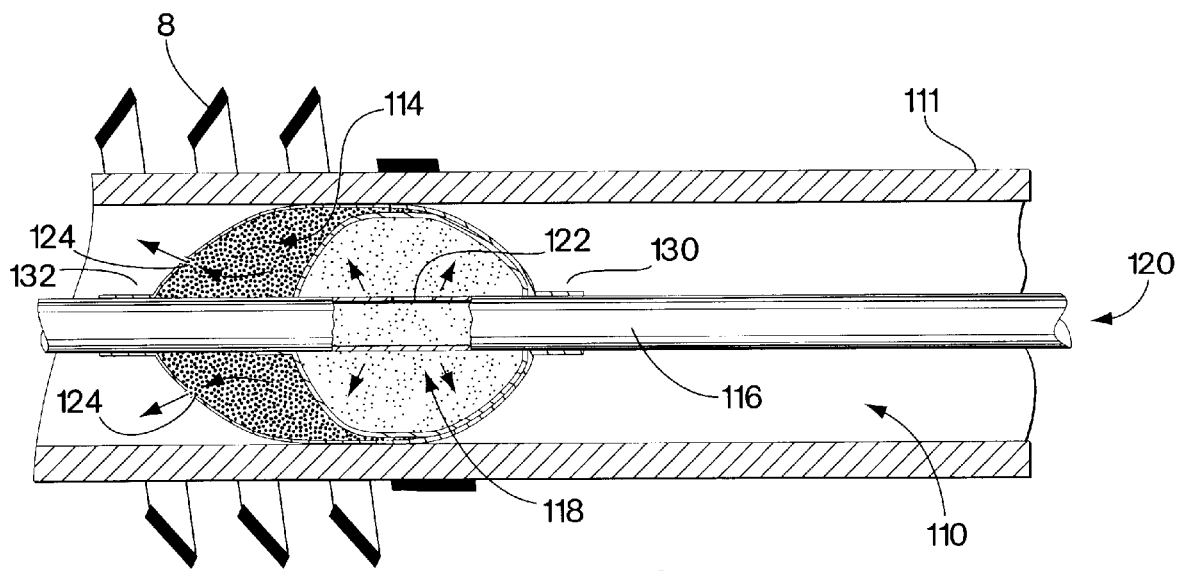

FIGS. 9A–9C show a double bladder therapeutic substance delivery system 110 that may be employed with the implant delivery systems of the present invention that can be configured to have an open lumen through their lengths. In particular the crinkle tube 22 and oval shaft 50 embodiments may be configured to employ the therapeutic substance delivery system 110. FIG. 9A shows a double bladder system 110 positioned within the central lumen 112 of a tube 111 of an implant delivery system similar to the crinkle tube delivery device. It is noted that other implant delivery sytems or catheter devices not disclosed herein may employ the therapeutic substance delivery system or the system could be deployed alone through a conventional catheter having a lumen.

The drug delivery system shown in FIGS. 9A–9C employs a first flexible bladder 114 filled with a therapeutic substance and mounted about a tube, 116 and in close longitudinal proximity to (FIG. 9B), or surrounding (FIG. 9C) a second flexible bladder 118 attached to the shaft 116 and inflatable with a conventional medium such as saline. The second bladder 118 is in fluid communication with a lumen 120 that extends through shaft 116 via a port 122. Expansion of the second bladder 118 within a confined space such as within a lumen 112 adjacent the first bladder 114 (FIG. 9B) or from within the first bladder (FIG. 9C) applies pressure to the first bladder, reducing its volume which increases fluid pressure in the first bladder sufficiently to cause the therapeutic substance to be ejected through tiny orifices 124 to the intended treatment site.

The bladders may be similar to a dilatation balloon in their shape, size and manner of attachment to the shaft 116. The bladders may be made from a strong but flexible material such as PVC or Nylon. The bladders may be approximately the same size so that volume reduction of the first bladder corresponds to the volume expansion of the second bladder. The first bladder may be filled with a therapeutic substance during the process of joining it the bladder to the shaft. After bonding the proximal neck 130 to the shaft, the catheter may be oriented so that the distal neck 132 is elevated. In this orientation, the therapeutic substance can be injected, by a syringe, inserted between the distal neck and the shaft, without the chance of the substance running out of the bladder or contaminating the bonding area between the distal neck and the shaft. After filling the bladder 114 with the substance, the distal neck is bonded to the shaft.

A plurality of tiny orifices 124 may be preformed in the drug bladder prior to use of the device and either prior or after being filled with the substance and bonded. Because the orifices are small, on the order of 0.001", and the substance within the first bladder is not pressurized it is expected that most therapeutic substances can be formulated to have a sufficiently high viscosity so that the substance will not leak out from the orifices in the absence of pressure applied by the second bladder. For this reason, an alternative method of prefilling the first bladder with a therapeutic substance may comprise the steps of piercing the surface of a bladder with a tiny syringe needle and injecting the substance through the bladder wall.

Another aspect of the invention utilizes electromagnetic guidance technology to provide a guidance system for use with an implant delivery system such as the systems discussed above. U.S. Pat. No. 5,769,843 (Abela), the entirety of which is incorporated herein by reference, discloses such a guidance system for positioning a laser catheter within the ventricle of the heart. An electromagnetic guidance system would be especially useful in the delivery of multiple mechanical implants to an area of ischemic myocardial tissue such as is described above. The delivery devices of the present invention may be equipped with two non-coplanar magnetic sensing coils in the distal ends of their shafts to cooperate with three sets of three magnetic fields generating external coils located outside the patient. The sensing coils of the catheter receive the electromagnetic field and thus, with assistance with from a computer can be located within the patient.

From the foregoing, it will be appreciated that the invention provides delivery devices for delivering implants and therapeutic substances to the myocardium. The invention is particularly advantageous for delivering devices and therapeutic substances to promote TMR and angiogenesis within ischemic myocardial tissue. The implants are simple and readily insertable into the intended tissue location with a minimum of steps. The delivery systems are simple to operate to implant the devices quickly.

It should be understood, however, that the foregoing description of the invention is intended merely to be illustrative thereof and that other modifications, embodiments and equivalents may be apparent to those skilled in the art without departing from its spirit. Having thus described the invention what we desire to claim and secure by letters patent is:

What is claimed is:

1. A delivery device for a hollow implant comprising:
   a first elongate shaft having proximal and distal ends, a lumen; and
   at least one deformable surface adjacent to the distal end and common with the shaft that can be deformed to contact an inside surface of an implant and reformed to release the implant; and
   a second shaft slidable relative to the first shaft to deform the deformable surface.

2. An implant delivery device as defined in claim 1 wherein the deformable surface is a section of the shaft having an oval cross sectional shape that is deformable to have a circular cross-sectional shape.

3. An implant delivery device as defined in claim 2 further comprising:
   a cam slidable within the lumen of the shaft that is selectively engageable with the oval sections to deform the sections to a round cross-sectional shape.

4. An implant delivery device comprising:
   a first elongate shaft having proximal and distal ends, and
   a continuous collapsible sleeve having a proximal end and a distal end and being mounted at the distal end of the shaft such that it can be deformed to contact an inside surface of an implant and reformed to release an implant mounted thereon,
   a second shaft mounted at one end to the distal end of the sleeve and slidable relative to the first shaft to deform the collapsible sleeve.

5. An implant delivery device as defined in claim 4 wherein:
   the first shaft comprises a push tube mounted over the second shaft and slidable relative to the second shaft and joined to the proximal end of the sleeve such that longitudinal movement of the push tube relative to the second shaft places an axial load on the sleeve.

6. An implant delivery device as defined in claim 5 wherein movement of the push tube in a distal direction relative to the second shaft places the sleeve in axial compression resulting in collapse of the sleeve and the formation of multiple folds having peaks that define a diameter that is larger than the diameter of the unloaded sleeve.

7. A delivery device for a hollow implant comprising:
   a first elongate shaft having proximal and distal ends, a lumen; and
   at least one deformable surface adjacent to the distal end that can be deformed to contact an inside surface of an implant and reformed to release the implant,
   a second shaft slidable relative to the first shaft to deform the deformable surface
   an implant carried about the deformable surface.

8. A method of implanting an implant device in the human body comprising:
   providing a shaft generally circular in cross-sectional shape, having a lumen and proximal distal ends and at least one segment having an oval cross-sectional shape;
   placing a tubular implant over the shaft such that the inside diameter of the tube becomes caught on the oval section of the shaft;
   navigating the shaft and associated implant tube to the intended delivery site within a patient;
   advancing a shaft that deforms the oval segment to circular cross-sectional shape to permit the tubular implant to slide over the segment and off the shaft.

9. A method of implanting an implant device in the human body comprising:
   providing a shaft having a distal end and a collapsible sleeve having a surface mounted around its distal end;
   placing a hollow implant over the collapsible sleeve;
   placing an axial load on the sleeve to collapse it and cause the formation of a plurality of folds along its surface thereby engaging the interior of the implant;
   navigating the shaft and associated implant tube to the intended delivery site within a patient;
   placing the sleeve in tension to remove the folds and release the implant from engagement with the sleeve.

* * * * *

UNITED STATES PATENT AND TRADEMARK OFFICE
CERTIFICATE OF CORRECTION

PATENT NO. : 6,248,112 B1
DATED : June 19, 2001
INVENTOR(S) : Richard A. Gambale et al.

It is certified that error appears in the above-identified patent and that said Letters Patent is hereby corrected as shown below:

Title page,
Item [75] Inventors, delete John E. Ahern, Melrose, MA (US) and Michael Parascandola, Londonderry, NH (US).
Item [56] References Cited, add the following documents:
U.S. PATENT DOCUMENTS
| | | |
|---|---|---|
| 3,680,544 | 08/1972 | Shinnick et al. |
| 4,894,057 | 01/1990 | Howes |
| 5,180,366 | 01/1993 | Woods |
| 5,562,922 | 10/1996 | Lambert |
| 6,053,924 | 04/2000 | Hussein |

FOREIGN PATENT DOCUMENTS
| | | |
|---|---|---|
| 19703482 | 01/1997 | (DE) |
| 0 490 459 A1 | 06/1992 | (EP) |
| 0 830 873 A2 | 03/1998 | (EP) |
| 0 853 921 A2 | 07/1998 | (EP) |
| 0 953 320 A2 | 11/1999 | (EP) |
| WO 90/06723 | 06/1990 | (WO) |
| WO 94/27612 | 12/1994 | (WO) |
| WO 95/33511 | 12/1995 | (WO) |
| WO 96/20698 | 07/1996 | (WO) |
| WO 97/38730 | 10/1997 | (WO) |
| WO 97/42910 | 07/1997 | (WO) |
| WO 97/45105 | 12/1997 | (WO) |
| WO 98/23228 | 06/1998 | (WO) |

UNITED STATES PATENT AND TRADEMARK OFFICE
CERTIFICATE OF CORRECTION

PATENT NO. : 6,248,112 B1
DATED : June 19, 2001
INVENTOR(S) : Richard A. Gambale et al.

It is certified that error appears in the above-identified patent and that said Letters Patent is hereby corrected as shown below:

FOREIGN PATENT DOCUMENTS cont'd.
WO 98/29148  07/1998     (WO)
WO 99/21510  05/1999     (WO)
WO 99/53863  10/1999     (WO)

Signed and Sealed this

Twenty-first Day of May, 2002

Attest:

Attesting Officer

JAMES E. ROGAN
Director of the United States Patent and Trademark Office